US007411067B2

(12) United States Patent
Niddam-Hildesheim et al.

(10) Patent No.: US 7,411,067 B2
(45) Date of Patent: Aug. 12, 2008

(54) CRYSTALLINE FORMS OF GATIFLOXACIN

(75) Inventors: Valerie Niddam-Hildesheim, Even-Yeouda (IL); Shlomit Wizel, Petah Tiqva (IL); Greta Sterimbaum, Rishon-Lezion (IL); Ehud Amir, Ramat-Aviv (IL)

(73) Assignee: Teva Pharmaceutical Industries Ltd (IL)

( * ) Notice: Subject to any disclaimer, the term of this patent is extended or adjusted under 35 U.S.C. 154(b) by 621 days.

(21) Appl. No.: 10/462,945

(22) Filed: Jun. 16, 2003

(65) Prior Publication Data
US 2004/0038988 A1 Feb. 26, 2004

Related U.S. Application Data

(60) Provisional application No. 60/389,093, filed on Jun. 14, 2002, provisional application No. 60/423,338, filed on Nov. 1, 2002.

(51) Int. Cl.
*C07D 401/04* (2006.01)
*A61K 31/47* (2006.01)
(52) U.S. Cl. .................. 546/156; 514/312; 544/363
(58) Field of Classification Search ................ 546/156; 514/312; 544/363
See application file for complete search history.

(56) References Cited

U.S. PATENT DOCUMENTS 5,880,283 A 3/1999 Matsumoto et al.
6,413,969 B1 7/2002 Raghavan et al.

FOREIGN PATENT DOCUMENTS

| EP | 0 629 621 | 12/1994 |
| EP | 0805156 A1 * | 12/1995 |
| EP | 0805 156 A | 11/1997 |
| WO | WO 02/22126 A1 * | 3/2002 |
| WO | WO 03/086402 | 10/2003 |

OTHER PUBLICATIONS

John Haleblian et al "Pharmaceutical Applications of Polymorphism"; Journal of Pharmaceutical Sciences, vol. 58, No. 8, Aug. 1969—pp. 911-929.
John K. Haleblian "Characterization of Habits and Crystalline Modification of Solids and Their Pharmaceutical Applications"; Journal of Pharmaceutical Sciences, vol. 64, No. 8, Aug. 1975—pp. 1269-1288.
G. Michael Wall "Pharmaceutical Applications of Drug Crystal Studies", Pharmaceuctical Manufacturing, vol. 3, No. 2, Feb. 1986; pp. 33-42.

* cited by examiner

*Primary Examiner*—James O. Wilson
*Assistant Examiner*—Paul V. Ward
(74) *Attorney, Agent, or Firm*—Kenyon & Kenyon LLP

(57) ABSTRACT

Provided are two novel crystalline forms of gatifloxacin, denominated form O and form V, and methods for their preparation.

5 Claims, 6 Drawing Sheets

CRYSTALLINE FORMS OF GATIFLOXACIN

CROSS-REFERENCE TO RELATED APPLICATIONS

This application claims the benefit of U.S. Provisional Applications Ser. No. 60/389,093, filed Jun. 14, 2002, and Ser. No. 60/423,338, filed Nov. 1, 2002, the contents of which are incorporated herein by reference.

FIELD OF THE INVENTION

The present invent relates to novel crystal form of (±) 1-cyclopropyl-6-fluoro-1,4-dihydro-8-methoxy-7-(3-methyl-1-piperazinyl)-4-oxo-3-quinolinecarboxylic acid, commonly known as gatifloxacin. More specifically, the present invention relates to gatifloxacin in form "O", to gatifloxacin form "V", and to methods for making them.

BACKGROUND OF THE INVENTION

Many pharmaceutically active organic compounds can crystallize in different crystalline forms. That is, they can crystallize more than one type of molecular packing with more than one type of internal crystal lattice. The respective resulting crystal structures can have, for example, different unit cells. This phenomenon—identical chemical structure but different crystalline form—is referred to as polymorphism and the species having different molecular structures are referred to as polymorphs.

Many pharmacologically active organic compounds can also crystallize such that second, foreign molecules, especially solvent molecules, are regularly incorporated into the crystal structure of the principal pharmacologically active compound. This phenomenon is referred to as pseudopolymorphism and the resulting structures as pseudopolymorphs. When the second molecule is a solvent molecule, the pseudopolymorphs can be referred to as solvates.

However, it is generally not possible to predict whether a particular organic compound will form polymorphs or pseudopolymorphs, let alone predict the structure and properties of the polymorphs or pseudopolymorphs.

The discovery of a new crystalline form (polymorph or pseudopolymorph) of a pharmaceutically useful compound provides an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new polymorphs or pseudopolymorphs of a useful compound. For a general review of polymorphs and the pharmaceutical applications of polymorphs see G. M. Wall, *Pharm Manuf.* 3, 33 (1986); J. K. Haleblian and W. McCrone, *J. Pharm. Sci.*, 58, 911 (1969); and J. K. Haleblian, *J. Pharm. Sci.*, 64, 1269 (1975), all of which are incorporated herein by reference.

Crystalline forms can be influenced by controlling the conditions under which the compound is obtained in solid form. Solid state physical properties that can differ from one crystalline form to the next include, for example, the flowability of the milled solid. Various crystalline forms can be more or less hygroscopic. Absorption of atmospheric moisture by a compound in powder form can impede its ability to flow. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound that can vary from one crystalline form to the next is its rate of dissolution in aqueous media, e.g. gastric fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its stability during storage.

These practical physical characteristics are influenced by the conformation, orientation, and packing of molecules in the unit cell, which characterize a particular polymorphic or pseudopolymorphic form of a substance. A polymorphic form may have thermodynamic properties different from those of the amorphous material or another polymorphic form. Thermodynamic properties can be used to distinguish between various polymorphs or pseudopolymorphs. Thermodynamic properties that can be used to distinguish between polymorphs and pseudopolymorphs can be measured in the laboratory by such techniques as capillary melting point, thermogravimetric analysis (TGA), differential scanning calorimetry (DSC), and differential thermal analysis (DTA).

A particular crystalline form can also possess distinct spectroscopic properties that may be detectable by, for example, solid state $^{13}C$ NMR spectroscopy and infrared (IR) spectroscopy. This is particularly so in the case of solvates because of the presence of absorptions or resonances due to the second, foreign molecule.

(±)-1-Cyclopropyl-6-fluoro-1,4-dihydro-8-methoxy-7-(3-methyl-1-piperazinyl)-4-oxo-3-quinolenecarboxylic acid, commonly known as gatifloxacin, is a synthetic broad-spectrum antibacterial agent for oral or intravenous administration.

U.S. Pat. No. 5,880,283 discloses that gatifloxacin forms a hygroscopic hemihydrate. The hemihydrate (a pseudopolymorph) is reported to be easily formed upon crystallization of gatifloxacin from water-containing organic solvents. The hemihydrate reportedly has disadvantages for manufacturing of solid oral dosage forms, e.g. tablets. The patent further discloses a novel pseudopolymorph of gatifloxacin, the sesquihydrate, and presents thermal analysis and x-ray diffraction data for this crystalline form. The sesquihydrate is reported to be less hygroscopic and more stable in manufacturing.

U.S. Pat. No. 6,413,969 discloses at least 12 different polymorphs or pseudopolymorphs of gatifloxacin and discloses the x-ray powder diffraction diagrams of at least 10 of these. The hexahydrate, pentahydrate and sesquihydrate are crystallized directly from aqueous solvents. Other crystalline forms are crystallized from a molten phase or by solid-solid phase transformations. The pentahydrate form is, according to the disclosure of WO 02/22126 A1, the most thermodynamically stable form and has the lowest aqueous solubility at room temperature. The interrelationships between the twelve identified crystalline forms are given in the application.

SUMMARY OF THE INVENTION

In one aspect, the present invention relates to a novel crystalline form of gatifloxacin, denominated form O, characterized by x-ray reflections at about 8.40°, 10.80°, 20.0°, 20.4°, and 21.2°±0.2°2θ.

In another aspect, the present invention relates to a method of making gatifloxacin crystalline form O including the steps of: providing, at reflux, a solution of gatifloxacin in an approximately 1:1 v/v mixture of acetonitrile and ethanol; cooling the solution to a temperature between about 53° and about 56° C.; optionally seeding the solution with gatifloxacin; maintaining the seeded solution at a temperature between about 53° and about 56° C. for a first holding time, especially about 2 hours; cooling the solution to a temperature of about 5° C. at a cooling rate of about 4 to about 8 degrees per hour whereby a slurry (suspension) is obtained; optionally maintaining the slurry at about 5° C. or below for a second holding time, especially about 2 hours; and isolating gatifloxacin crystalline form O from the slurry.

In another aspect, the present invention relates to a method of making a mixture in about a 1:1 weight ratio of gatifloxacin form O and prior-art sesquihydrate including the step of exposing gatifloxacin in prior-art forms omega (Ω) or TE, or form C, to an atmosphere having a relative humidity of at least about 60% (form C), or at least about 80% (form TE and omega) for an exposing time, especially at least about 24 hours to 2 weeks, most especially about 1 week.

In another aspect, the present invention relates to a method of making a mixture of gatifloxacin form O and gatifloxacin sesquihydrate in about an 80:20 weight ratio comprising the step of exposing gatifloxacin form C for an exposure time to an atmosphere having a relative humidity of at least about 60%.

In still a further aspect, the present invention relates to a method of making a mixture of gatifloxacin form O and gatifloxacin sesquihydrate in about a 1:1 weight ratio comprising the step of exposing gatifloxacin form omega for an exposure time to an atmosphere having a relative humidity of at least about 60%.

In yet a further aspect, the present invention relates to a method of making a mixture of gatifloxacin form O and gatifloxacin sesquihydrate in about a 1:1 weight ratio comprising the step of exposing gatifloxacin form TE for an exposure time to an atmosphere having a relative humidity of at least about 80%.

In still another aspect, the present invention relates to a crystalline form of gatifloxacin, denominated form V, characterized by x-ray reflections at about 6.0°, 14.1°, 21.1° and 22.5°±0.2° 2θ and typically having a water content of about 1 wt-% to about 3 wt-%.

In yet still a further embodiment, the present invention relates to a method of making gatifloxacin crystalline form V including the steps of: providing, at reflux, a solution of gatifloxacin in acetonitrile; cooling the solution to ambient temperature at a cooling rate of at least about 1° C. per minute whereby a suspension is obtained; further crash cooling the suspension to about 5° C. or less; isolating the solid from the suspension; and treating the isolated solid with moist gas, especially moist air in a fluidized bed apparatus to obtain form V.

DETAILED DESCRIPTION OF THE INVENTION

The present invention provides novel crystalline forms (polymorphs and/or pseudopolymorphs) of gatifloxacin, [(±) 1-cyclopropyl-6-fluoro-1,4-dihydro-8-methoxy-7-(3-methyl-1-piperazinyl)-4-oxo-3-quinolinecarboxylic acid]. The novel crystalline forms are denominated form "O" and form "V", respectively. The present invention further provides methods of making the novel crystal forms, as well as mixtures of novel form O with prior-art sesquihydrate.

As used herein in connection with a measured quantity, the term about refers to that variation in the measured quantity as would be expected by the skilled artisan making the measurement and exercising a level of care commensurate with the objective of the measurement and the precision of the measuring equipment used.

As used herein, atmospheric pressure refers to the prevailing atmospheric pressure between about 740 and about 780 mm. Hg.

As used herein, the term ambient temperature is a temperature between about 18° and about 30° C.

As used herein in connection with the present invention, x-ray diffraction refers to x-ray diffraction by the powder diffraction technique. X-ray powder diffraction analysis was performed using a Scintag powder diffractometer with variable goniometer, a Cu source, and a solid state detector. A standard round aluminum sample holder with zero background quartz plate was used. Samples were scanned from 2° to 40° 2θ at 3° per minute in the continuous scan mode. Reflections are reported as peak maxima in the intensity vs. 2θ plots, and are subject to the normal experimental error (uncertainty). Samples were promptly analyzed "as is".

Differential scanning calorimetry (DSC) was performed using a Mettler Toledo model 821$^e$ instrument at a heating rate of 10° C. per minute. Sample weights were between 3 and 5 mg and were contained in standard crucible having 3-holed covers.

Thermogravimetric analysis (TGA) was performed using a Mettler TG50 thermobalance. Samples of 7 to 15 milligrams were analyzed at a heating rate of 10° per minute.

As used herein, LOD refers to loss on drying as determined by TGA.

Water content was determined by the Karl-Fisher method.

The skilled artisan will recognized that, as used herein, the terms slurry and suspension are synonymous.

In one embodiment, the present invention provides a novel crystalline form of gatifloxacin, designated form O, that can be characterized by x-ray reflections at about 8.4°, 10.8°, 20.0° 20.4°, and 21.2°+/−0.2° 2Θ. A typical x-ray diffraction diagram for gatifloxacin form O is given in FIG. 1.

Figure 3:
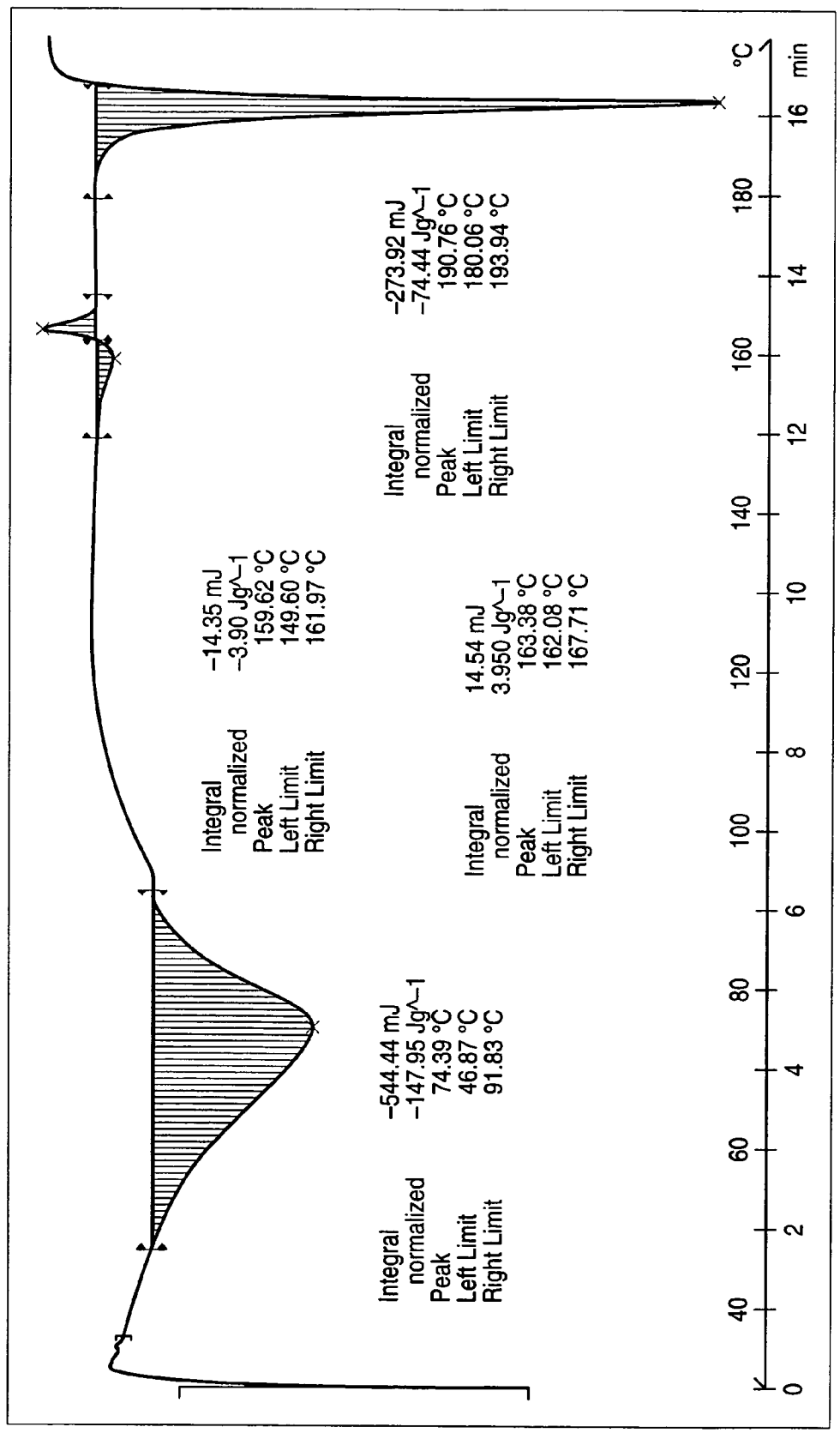
FIG. 3 shows a typical DSC thermogram for gatifloxacin form O.
Figure 4:
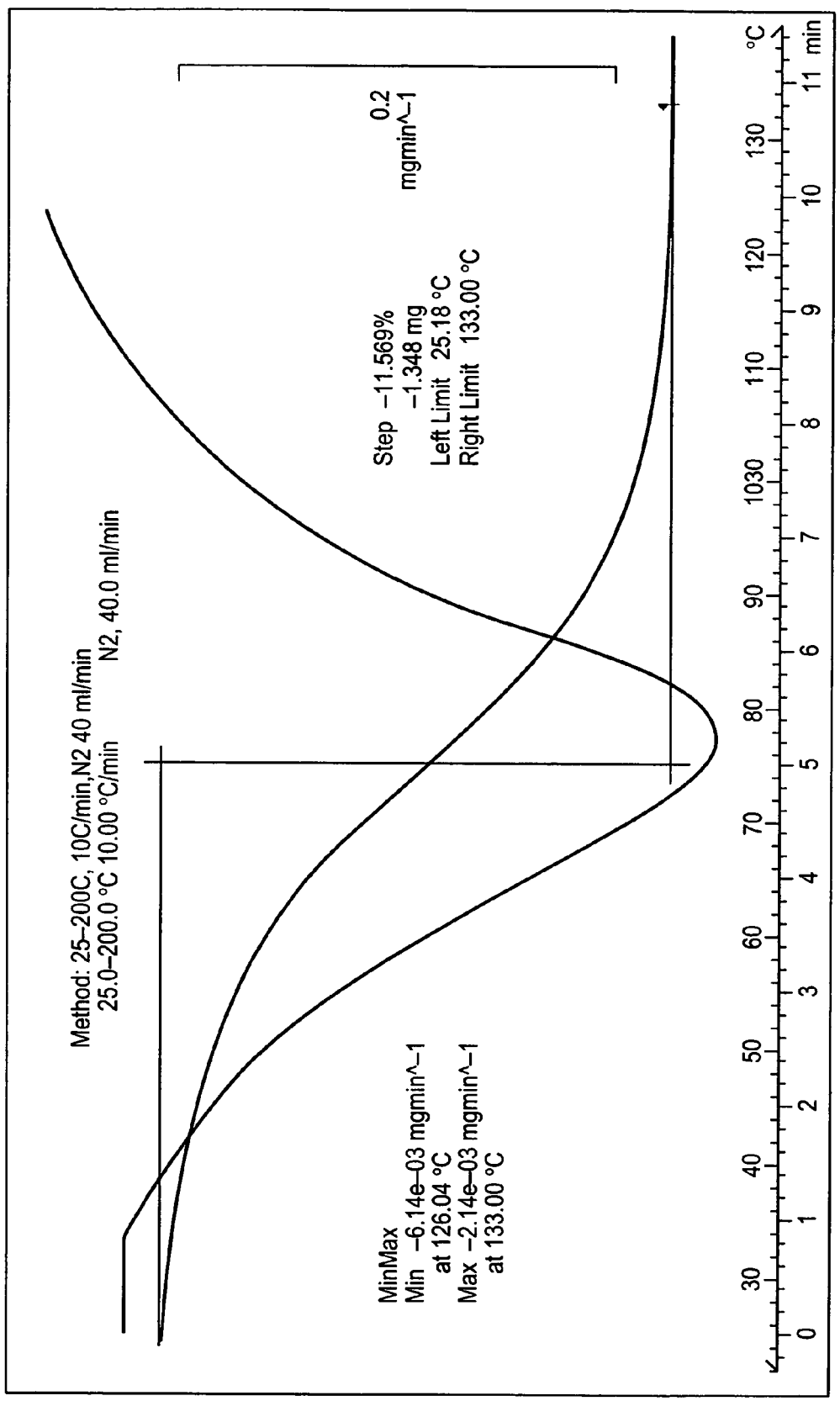
FIG. 4 shows a typical TGA thermogram for gatifloxacin in form O.

FIG. 4 shows a typical TGA thermogram for gatifloxacin form O. According to TGA analysis, form O loses between about 10% and about 15% (11.6% in this example) of its weight up to a temperature of about 120° C. The water content by Karl-Fisher analysis is about 11.8%. This water content corresponds approximately to the calculated value for gatifloxacin trihydrate. FIG. 3 shows a typical DSC thermogram for gatifloxacin form O.

In another embodiment, the present invention provides a method for making gatifloxacin form O that includes the step of crystallizing gatifloxacin from solution in a mixed solvent that includes ethanol (EtOH) and acetonitrile (ACN). The preferred mixed solvent is made-up of approximately equal volumes of ethanol and acetonitrile.

Gatifloxacin is dissolved in the mixed solvent at a temperature of at least about 75° C., preferably at reflux. In preferred embodiments, the solution is refluxed for a reflux time of about one-half hour. The solution is then cooled, with agitation, to a first holding temperature between about 52° and 57° C., preferably between about 53° and about 56° C. The cooled mixture can be and preferably is seeded with crystals of gatifloxacin. The mixture can be and preferably is held at a temperature between about 52° and about 57° C. for a second holding time of about one-half to about 3 hours. Two hours is the preferred seeding time.

Whether or not a first holding time is employed, the mixture is then cooled, with agitation, to a temperature of about 5° C. or less at a cooling rate between about 4° and about 8°, preferably about 6° C., per hour whereby a slurry (suspension) is obtained. The slurry can be and preferably is maintained, with agitation, at a temperature of about 5° C. or less for a second holding time of about one-half to about 3 hours. Two hours is the preferred holding time.

Gatifloxacin form O can be isolated from the slurry by any means known in the art, for example filtration (gravity or suction) or centrifugation, to mention just two. The crystal form of the gatifloxacin so obtained is confirmed by x-ray analysis "as is".

In another embodiment, the present invention provides a method of making a mixture of novel crystalline form O and prior-art sesqihydrate. The ratios will depend, inter alia, on the conditions of treatment. The mixtures can be made by exposing prior art forms omega or TE, or crystalline form C (characterized by x-ray reflections at 7.2°, 10.8°, 15.8°, 21.8°, and 26.2°±0.2° 2θ) to an atmosphere having a relative humidity of at least about 60% (form c), or at least about 80% (form TE and omega) for an exposing time. The exposing time will generally be between about 24 hours and two weeks.

Form C is the subject of copending U.S. patent application filed May 12, 2003 under Ser. No. 10/436,736 and can be made as described in the examples below.

Preferably, the form omega, TE, or C is exposed as a thin layer of particles or crystals to facilitate diffusion of gasses and vapors. Preferably, the exposing is at ambient temperature.

Figure 2:
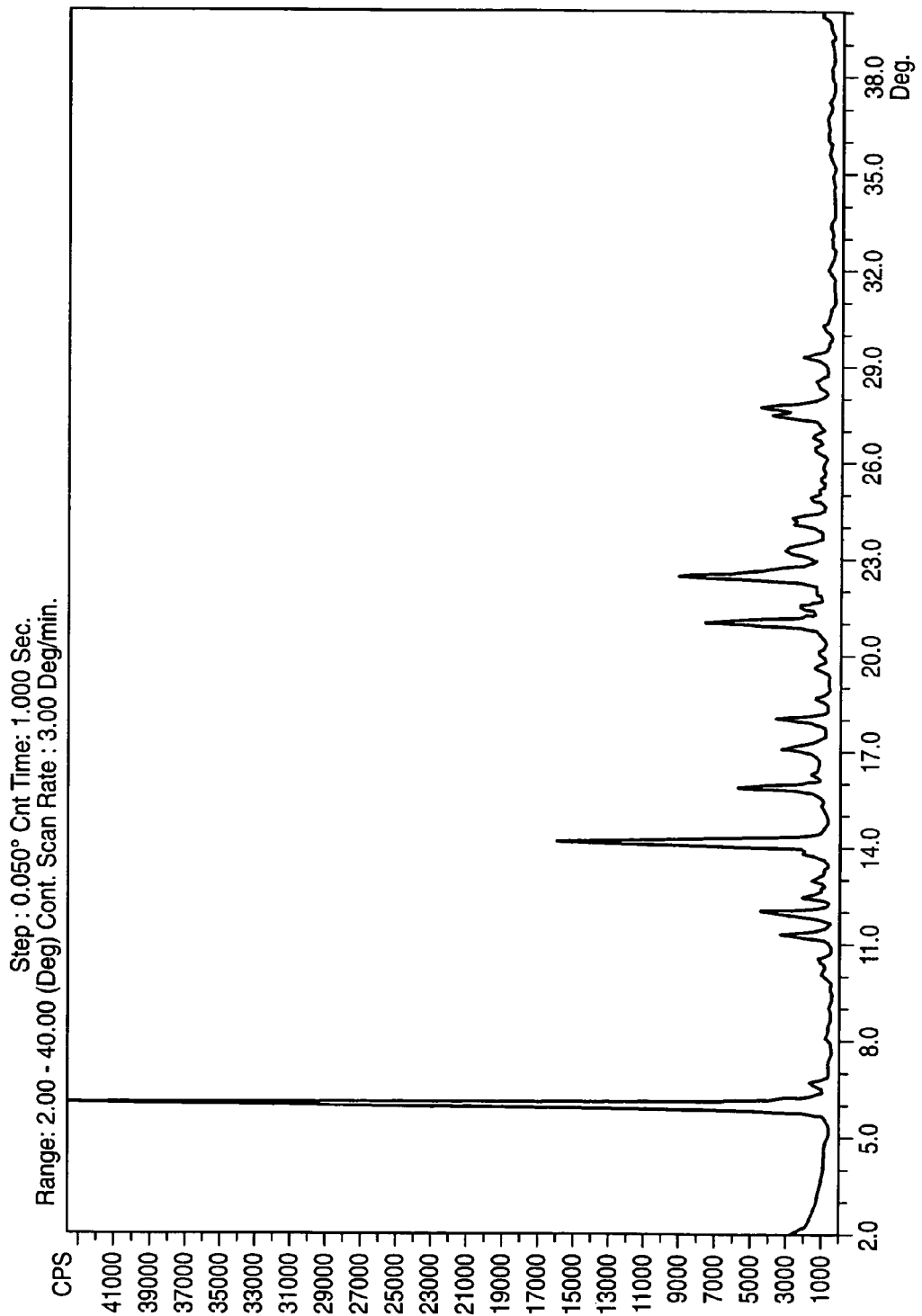
FIG. 2 shows a typical x-ray diffraction diagram for gatifloxacin form V.

In a further embodiment, the present invention provides a novel crystalline form of gatifloxacin, denominated form V, characterized by x-ray reflections at about 6.0°, 14.1°, 21.1°, and 22.5°±0.2°2θ FIG. 2 shows a typical x-ray diffraction diagram of form V.

Figure 5:
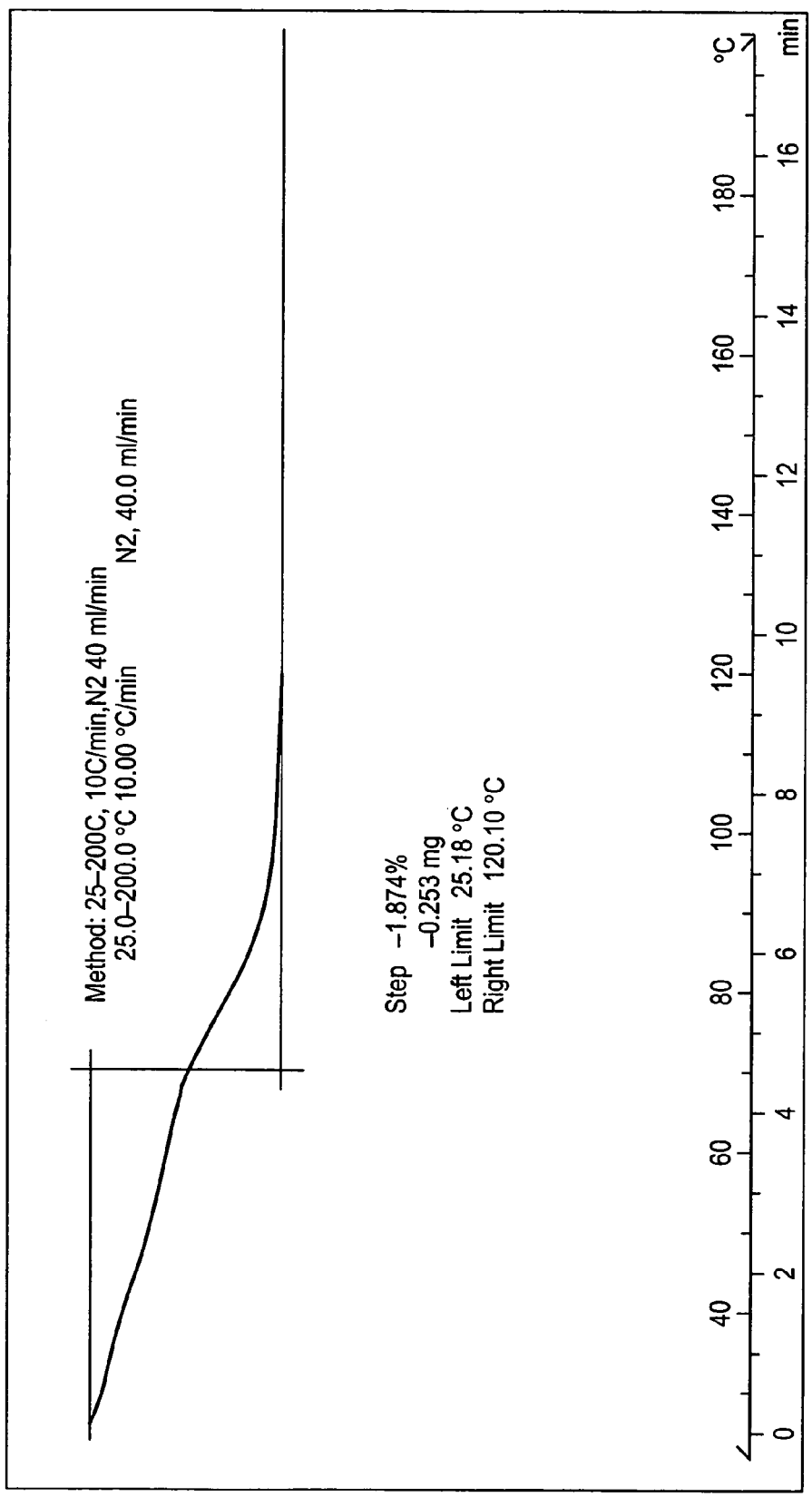
FIG. 5 shows a typical TGA thermogram for gatifloxacin form V.
Figure 6:
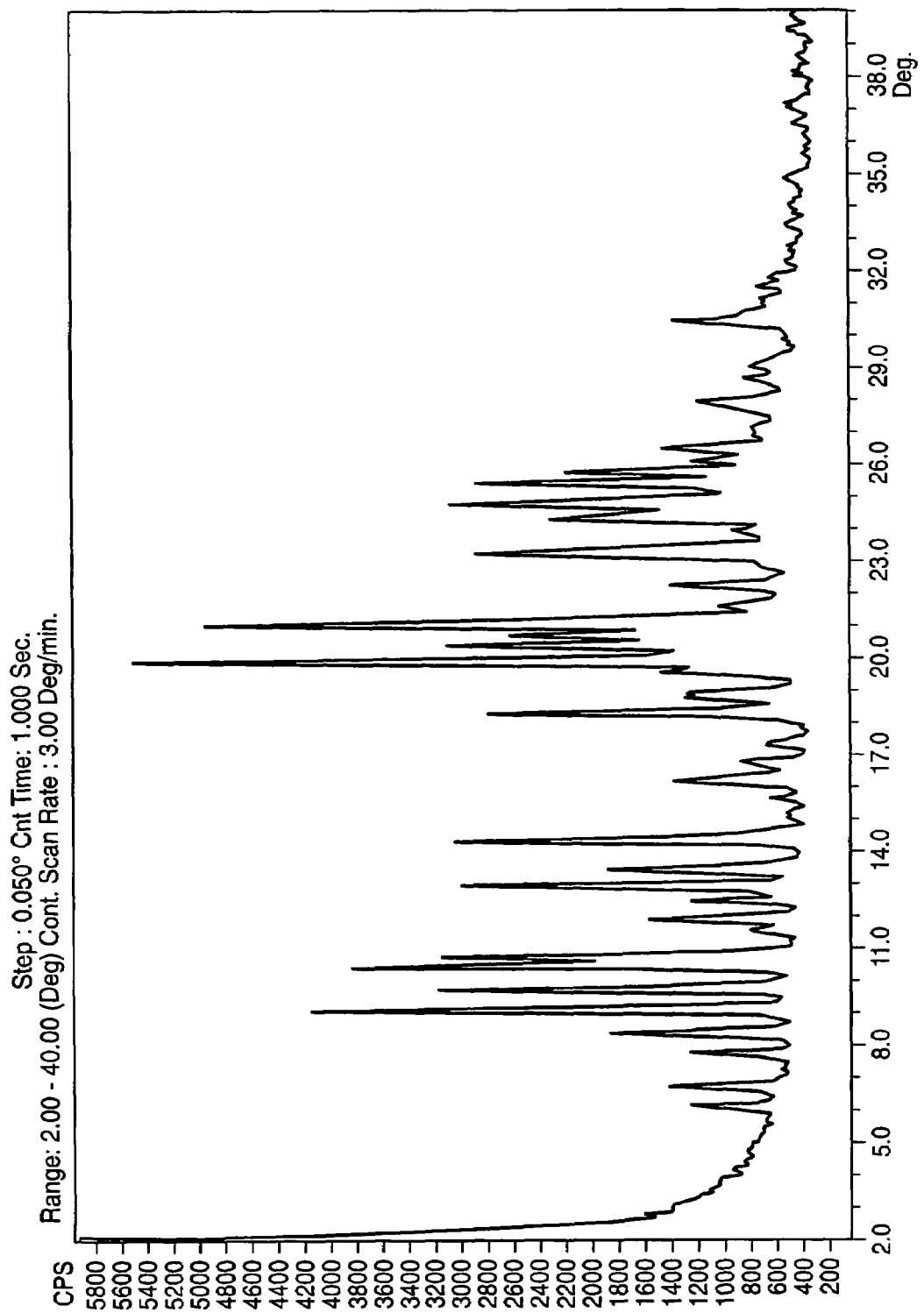
FIG. 6 shows a typical x-ray diffraction diagram of about a 1:1 by weight mixture (50:50) of form O and gatifloxacin sesquihydrate.

Gatifloxacin form V typically has a water content of between about 1% and about 3% by weight. The TGA of gatifloxacin form V shows a weight loss of between about 4% and about 5%. A typical TGA thermogram of form V is shown in FIG. 5.

In another embodiment, the present invention provides a modified crystallization method for making gatifloxacin form V, the solution is rapidly cooled from reflux, and formation of form V is completed in a subsequent drying step in which the product from crystallization is treated with a moist gas, preferably moist air, in a suitable apparatus, for example a fluidized bed apparatus. The cooling step should be carried-out at about 1° C. per minute.

The product from crystallization, which can be a mixture of forms, can be made by cooling, with agitation, a solution of gatifloxacin in acetonitrile from reflux to ambient temperature at a cooling rate of at least about 1° C. per minute. The resulting mixture is then crash-cooled, with agitation, to a temperature of about 5° C. or less. By crash cooling it is meant the mixture is cooled as rapidly as possibly by applying a static or dynamic cooling medium to the outside of the vessel in which the mixture is contained.

In another embodiment, the present invention provides pharmaceutical compositions including gatifloxacin in form O and at least one pharmaceutically acceptable excipient.

In yet another embodiment, the present invention provides pharmaceutical compositions including gatifloxacin form V and at least one pharmaceutically acceptable excipient.

The pharmaceutical composition can be in the form of a solid oral dosage form (e.g. compressed tablets or capsules), or it can be in the form of a liquid oral dosage form, e.g. a solution or oral suspension.

Compressed tablets can be made by dry or wet granulation methods as is known in the art. In addition to the pharmaceutically active agent or drug, compressed tablets contain a number of pharmacologically inert ingredients, referred to as excipients. Some excipients allow or facilitate the processing of the drug into tablet dosage forms. Other excipients contribute to proper delivery of the drug by, for example, facilitating disintegration.

Excipients can be broadly classified according to their intended function. However, it must be kept in mind that a particular excipient can function in more than one way.

Diluents increase the bulk of a solid pharmaceutical composition and may make a pharmaceutical dosage form containing the composition easier for the patient and caregiver to handle. Diluents for solid compositions include, for example, microcrystalline cellulose (e.g. AVICEL®, microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch. The dissolution rate of a compacted solid pharmaceutical composition in the patient's stomach may be increased by the addition of a disintegrant to the composition.

Disintegrants include alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Of course, wet or dry granulate can also be used to fill capsules, for example gelatin capsules. The excipients chosen for granulation when a capsule is the intended dosage form may or may not be the same as those used when a compressed tablet dosage form is contemplated.

Selection of excipients and the amounts to use may be readily determined by the formulation scientist based upon experience and consideration of standard procedures and reference works in the field.

The present invention can be further illustrated with the following non-limiting examples. In the following examples, the polymorphic or pseudopolymorphic form of gatifloxacin was determined by x-ray diffraction.

EXAMPLE 1

Gatifloxacin Form O

A 0.5 liter reactor equipped with mechanical stirrer, condenser and thermometer, was charged with GTF-crude dry (50 g), ACN (187.5 mL) and EtOH (187.5 mL). The slurry was then heated to reflux (75° C.) and stirred at a rate of 400 rpm. The heating was continued for 0.5 hours until getting a clear solution. Then the clear solution was cooled to 53-56° C. and was seeded with 0.1 g of GTF. At the end of the addition the stirring was maintained for 2 hours at 53-56° C. then cooled during 8 hours until 5° C. and maintained with the stirring for 2 hours at this temperature.

The slurry was filtered under vacuum and washed with 75 mL of a mixture ACN:EtOH 1:1 to obtain 59.5 g of wet material. The solvent-wet sample was analyzed "as-is" by XRD and found to be form O.

EXAMPLE 2

Gatifloxacin Form V

A 250 mL flask equipped with mechanical stirrer, condenser and thermometer, was charged with GTF-crude dry (15 g) and ACN (144 mL). The solution was heated to reflux and stirred at this temperature for 30 minutes. The clear solution was then cooled suddenly to ambient temperature over 50 minutes by removing the flask from the oil bath and then immediately thereafter cooled to 5° C. with an ice bath.

The resulting slurry was maintained at this temperature for 1 hour. The slurry was filtered under vacuum and washed with 25 mL of ACN. The wet sample was analyzed by XRD and found to be a mixture of forms V and E1.

A portion of the wet material was treated in a fluidized bed drier at 50° C. for 45 min. with a wet atmosphere to obtain gatifloxacin crystals. The treated sample was analyzed by XRD and found to be gatifloxacin form V.

EXAMPLE 3

Form O and Sesquihydrate

Gatifloxacin in form Ω (200 mg powder) was spread as a thin layer in a container having short vertical walls. The container was placed in a controlled humidity cell at 100% RH for 1 week. The powder was found to be a an approximately equal weight (1:1) mixture of form O and sesquihydrate.

EXAMPLE 4

Form O and Sesquihydrate

Gatifloxacin in form Ω (200 mg powder) was spread as a thin layer in a container having short vertical walls. The container was placed in a controlled humidity cell at 80% RH for 1 week. The powder was found to be a an approximately equal weight (1:1) mixture of form O and form Ω.

EXAMPLE 5

Gatifloxacin in form C (200 mg powder) was spread as a thin layer in a container having short vertical sides. The container was placed in a controlled humidity cell at 100% RH for two weeks. The powder was found to be a mixture of form O and sesquihydrate.

EXAMPLE 6

Form O and Sesquihydrate

Gatifloxacin in form C (200 mg powder) was spread as a thin layer in a container having short vertical sides. The container was placed in a controlled humidity cell at 80% RH for two weeks. The powder was found to be an approximately 30:70 mixture by weight of form O and sesquihydrate.

EXAMPLE 8

Form C and Sesquihydrate

Gatifloxacin in form C (200 mg powder) was spread as a thin layer in a container having short vertical sides. The container was placed in a controlled humidity cell at 60% RH for two weeks. The powder was found to be an approximately 80:20 mixture by weight of form C and form O.

EXAMPLE 8

Form O and Sesquihydrate

Gatifloxacin in form TE (200 mg powder) was spread as a thin layer in a container having short sides. The container was placed in a controlled humidity cell at 100% RH for 2 weeks. The powder was found to be a an approximately equal weight (1:1) mixture of form O and sesquihydrate.

EXAMPLE 9

Form O and Sesquihydrate

Gatifloxacin in form TE (200 mg powder) was spread as a thin layer in a container having short sides. The container was placed in a controlled humidity cell at 80% RH for 2 weeks. The powder was found to be an approximately equal weight mixture (1:1) of form O and sesquihydrate.

EXAMPLE 10

Form C 5 g of gatifloxacin were suspended in 40 mL of 1-butanol. The mixture was heated to reflux temperature until complete dissolution of the material. The solution was then stirred at this temperature for 5 minutes, cooled to ambient temperature, and then to 5° C. The stirring was maintained at this temperature for one hour and then the mixture was filtered under vacuum. The solid obtained was put in an atmospheric oven at 60° C. for 40 hours.

The sample was analyzed by PXRD and found to be form C.

We claim:

1. Crystalline gatifloxacin form O having the following chemical formula

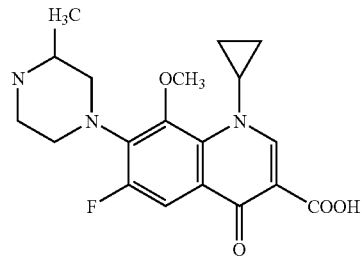

characterized by x-ray reflections at about 8.4°, 10.8°, 20.0°, 20.4°, and 21.2°±0.2°2θ.

Figure 1:
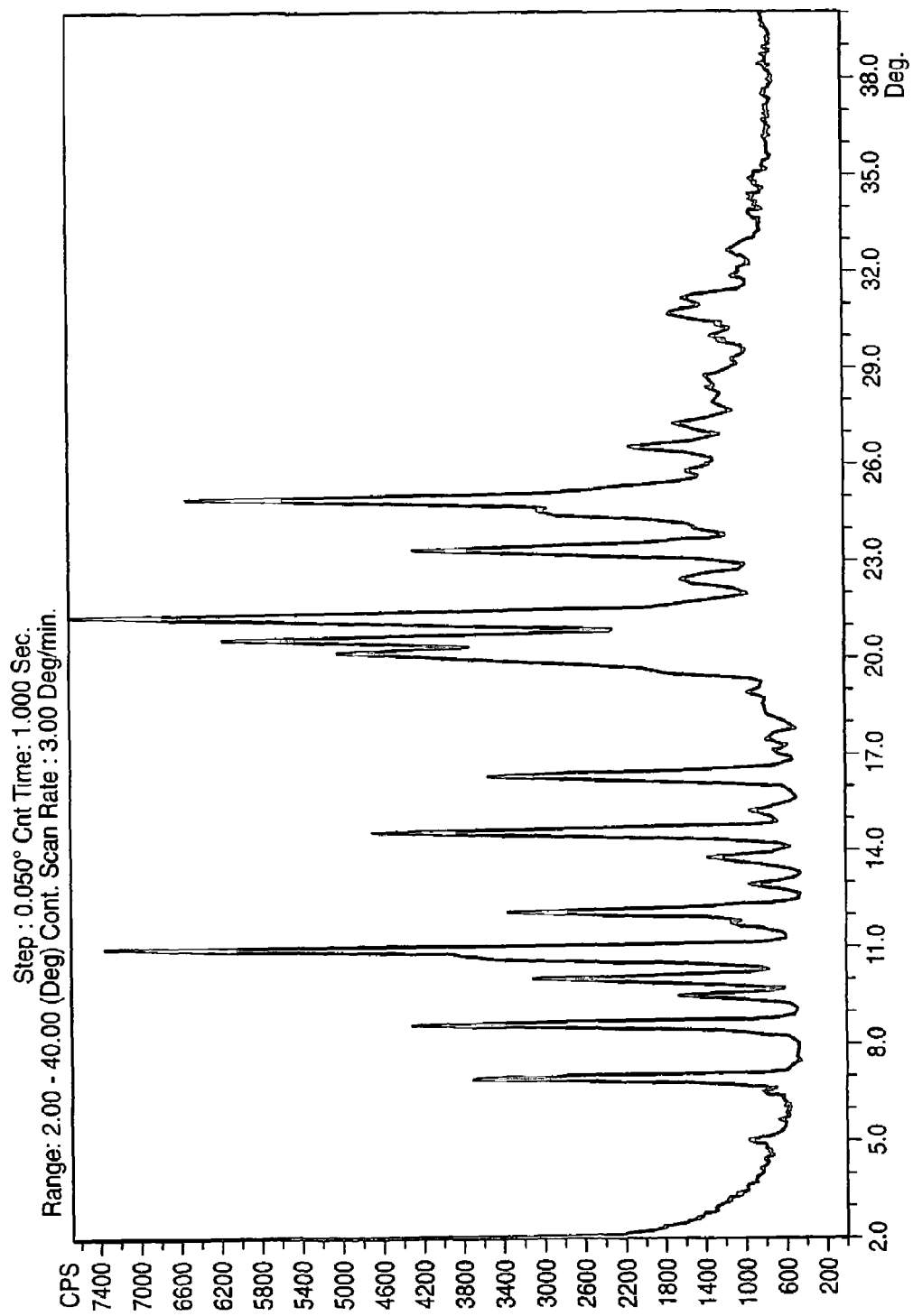
FIG. 1 shows a typical x-ray diffraction diagram for gatifloxacin form O.

2. The crystalline form of gatifloxacin of claim 1 having an x-ray diffraction diagram as shown in FIG. 1.

3. The crystalline form of gatifloxacin of claim 2 having a DSC thermogram as shown in FIG. 3.

4. The crystalline form of gatifloxacin of claim 1 having a water content of about 10% to about 15% by weight.

5. A pharmaceutical composition comprising the gatifloxacin of claim 1 and at least one pharmaceutically acceptable excipient.

* * * * *